(12) United States Patent
Danko

(10) Patent No.: US 6,774,991 B1
(45) Date of Patent: *Aug. 10, 2004

(54) METHOD AND APPARATUS FOR INSPECTING A PATTERNED SEMICONDUCTOR WAFER

(75) Inventor: Joseph J. Danko, Shrewsbury, MA (US)

(73) Assignee: Inspex Incorporated, Billerica, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/579,593

(22) Filed: May 26, 2000

Related U.S. Application Data (63) Continuation-in-part of application No. 09/518,977, filed on Mar. 4, 2000.
(60) Provisional application No. 60/136,257, filed on May 27, 1999.

(51) Int. Cl.[7] .................. G01N 21/00; G01N 21/86; G01N 21/88
(52) U.S. Cl. .................. 356/237.4; 356/237.5; 250/559.41; 250/559.45
(58) Field of Search .................. 356/237.4, 237.5, 356/237.3; 250/559.41, 559.45; 242/120; 348/126

(56) References Cited

U.S. PATENT DOCUMENTS

| | | |
|---|---|---|
| 4,772,126 A | 9/1988 | Allemand et al. |
| 4,895,446 A | 1/1990 | Maldari et al. |
| 4,898,471 A | 2/1990 | Stonestrom et al. |
| 4,966,457 A | 10/1990 | Hayano et al. |
| 5,046,847 A | 9/1991 | Nakata et al. |
| 5,264,912 A * | 11/1993 | Vaught et al. ............. 250/550 |
| 5,355,212 A | 10/1994 | Wells et al. |
| 5,625,193 A | 4/1997 | Broude et al. |
| 5,659,390 A | 8/1997 | Danko |
| 5,818,576 A * | 10/1998 | Morishige et al. ...... 250/559.45 |
| 5,854,671 A * | 12/1998 | Nishi ............................ 355/53 |
| 6,020,957 A * | 2/2000 | Rosengaus et al. ....... 356/237.4 |
| 6,078,386 A * | 6/2000 | Tsai et al. ................. 356/237.1 |
| 6,091,488 A * | 7/2000 | Bishop .................... 356/237.5 |
| 6,201,601 B1 * | 3/2001 | Vaez-Iravani et al. ... 356/237.4 |
| 6,288,780 B1 * | 9/2001 | Fairley et al. ........... 356/237.1 |
| 6,366,352 B1 * | 4/2002 | Goldberg et al. ......... 356/237.2 |
| 6,587,193 B1 * | 7/2003 | Reinhron et al. ........ 356/237.5 |

* cited by examiner

Primary Examiner—Zandra V. Smith
Assistant Examiner—Gordon J. Stock, Jr.
(74) Attorney, Agent, or Firm—Kriegsman & Kriegsman (57) ABSTRACT

A method and apparatus for inspecting a surface of a semiconductor wafer having repetitive patterns for contaminant particles using scattered light which involves directing two beams of light at different approach angles onto the surface in a manner so as to illuminate two intersecting stripe shaped regions on the surface. An imaging lens collects scattered light from the surface as the semiconductor wafer is moving and then images the scattered light collected onto a CCD camera having a square array sensor and arranged to operate in a time delayed integration (TDI) mode. The field of view of the CCD camera is centered at the intersection of the two striped regions. Each light beam striking the surface produces a Fourier diffraction pattern of scattered light in the back focal plane of the imaging lens. In setting up the apparatus, the angle of incidence of one of the light beams is adjusted to shift one of the diffraction patterns, if necessary, so that it overlaps the other diffraction pattern. If the two approach angles are symmetrically disposed, then the two diffraction patterns overlap and adjustment of the angle of incidence of one of the beams is not necessary.

17 Claims, 9 Drawing Sheets

METHOD AND APPARATUS FOR INSPECTING A PATTERNED SEMICONDUCTOR WAFER

CROSS-REFERENCE TO RELATED APPLICATIONS

This application claims the priority of provisional patent application serial No. 60/136,257, which was filed on May 27, 1999 in the name of Joseph J. Danko and is a continuation-in-part of U.S. patent application Ser. No. 09/518,977 filed on Mar. 4, 2000 in the name of Joseph J. Danko.

BACKGROUND OF THE INVENTION

The present invention relates generally to the inspection of semiconductor wafers and more particularly, to a method and apparatus for inspecting a surface of a semiconductor wafer having repetitive patterns for pattern defects and/or contaminant particles.

Integrated circuits (ICs) are commonly manufactured through a series of processing steps. Very often more than a hundred processing steps are performed to produce a properly functioning integrated circuit chip.

A semiconductor material, commonly in the shape of a wafer, serves as the substrate for integrated circuits. Semiconductor ICs are typically manufactured as an assembly of a hundred or more chips on a single semiconductor wafer, which is then cut up to produce the individual IC chips. Typically, a wafer made of silicon is used as the integrated circuit substrate, the silicon wafer being approximately 150–200 mm in diameter and 0.5–1 mm thick. During the manufacturing process, the silicon wafer is first polished and cleaned to remove any contaminant particles situated thereon. The silicon wafer is then is treated in preparation for a series of processing steps involving a plurality of photolithographic patterns (also commonly referred to as masks). In the production of integrated circuits, microelectronic circuits are formed onto the silicon wafer through a process of layering. In the layering process, conductive and insulative layers of thin films are deposited and patterned onto the silicon wafer. Each layer is patterned by a mask designed specifically for it, the mask defining the areas within the wafer that are to be treated such as by etching or implanting.

Semiconductor fabrication technology today deals with silicon wafers which are approximately 200 mm in diameter and which feature geometries with dimensions well below 1 μm (micrometer). Due to the high complexity and level of integration of integrated circuits, the absence of contaminants on every layer of the wafer is critical in order to realize acceptable levels of product yield. However, it has been found that contaminant particles are often introduced onto the semiconductor wafer during the manufacturing process of integrated circuits. As a consequence, the presence of one contaminant particle larger than the half the width of a conductive line on the silicon wafer can result in complete failure of a semiconductor chip produced from the wafer. Such a wafer has to be discarded which thereby decreases the percentage yield per wafer and increases the overall cost of the individual chips. Therefore, a critical task facing semiconductor process engineers is to identify and, as far as possible, to eliminate sources of surface contamination on each layer of the semiconductor wafer.

Accordingly, inspection systems are well known in the art and are commonly used to detect, view, identify and correct yield limiting defects introduced in the fabrication process of integrated circuits. Wafer inspection systems often include a light source, such as a laser, and a light sensitive imaging camera, or detector. In use, the light source is used to scan the surface of the wafer by means of illuminating particular regions of the surface of the wafer. The light sensitive imaging camera is positioned relative to the wafer to pick up scattered light for display on a viewing screen for further analysis. The imaging camera creates a visual for the viewing screen based on the number of photons which disperse from the wafer as the laser performs its scanning function. The visual could equivalently be formed by use of a non-imaging detector (e.g. a photomultiplier tube) with appropriate means of scanning for image formation. The camera will detect light scattered from any contaminant particles situated on the wafer, the intensity of the scattered light being generally proportional to the size of the particles, wherein the larger particles generally reflect more photons onto the imaging camera than smaller particles. As a consequence, larger particles will produce a brighter image and will have a greater light intensity than smaller particles.

Inspection systems of the type described above have been made commercially available by such companies as Inspex, Inc. of Billerica, Mass.

In U.S. Pat. No. 4,772,126 to C. D. Allemand et al, there is disclosed an apparatus and method for detecting the presence of particles on the surface of an object such the front side of a patterned semiconductor wafer. A vertically expanded, horizontally scanning, beam of light is directed onto an area on the surface of the object at a grazing angle of incidence. A video camera positioned above the surface detects light scattered from any particles which may be present on the surface, but not specularly reflected light. The surface is angularly prepositioned (rotated) relative to the incident light beam so that the diffracted light from the surface and the pattern of lines on the surface is at a minimum. The object is then moved translationally to expose another area to the incident light beam so that the entire surface of the object or selected portions thereof can be examined, an area at a time.

In U.S. Pat. No. 4,895,446 to M. A. Maldari et al. an apparatus and method are disclosed for detecting the presence of particles on the surface of an object such as the front side of a patterned semiconductor wafer. A collimated beam of light is directed onto an area on the surface of the object at a grazing angle of incidence. A detector positioned above the surface detects light scattered from any particles which may be present on the surface, but not specularly reflected light. The output of the detector is fed into a computer where the information is processed and then displayed on a display. The surface is prepositioned relative to the incident light beam so that the diffracted light from the surface and the pattern on the surface is at a minimum. The object is then moved translationally too expose another area to the incident light beam so that the entire surface of the object or selected portions thereof can be examined, an area at a time.

In U.S. Pat. No. 5,659,390 to J. J. Danko, there is disclosed a method and apparatus for detecting particles on a surface of a semiconductor wafer having repetitive patterns. The apparatus for detecting particles on the front surface of a patterned semiconductor wafer having repetitive patterns includes a laser for illuminating an area on the front surface at grazing angle of incidence with a beam of polarized light. A lens collects light scattered from the area and forms a Fourier diffraction pattern of the area illuminated. A Fourier mask blocks out light collected by the lens at locations in the Fourier diffraction pattern where the intensity is above a predetermined level indicative of background information and leaves in light at locations where the intensity is below the threshold level indicative of possible particle information. The Fourier mask includes an optically addressable spatial light modulator and a crossed polarizer with the Fourier diffraction pattern being used as both a read beam and a write beam for the spatial light modulator. A camera detects scattered light collected from the area by the lens and not blocked out by the Fourier mask.

Although widely used in commerce, inspection systems of the type described above have been found, on occasion, to be unsatisfactory in detecting the majority of notable particles disposed on the substrate. Rather, inspection systems of the type described above have been found, on occasion, to detect only a small fraction of the total number of notable defects on the substrate, which is highly undesirable.

The effectiveness in which an inspection system can detect particles on a substrate is dependent upon certain characteristics. As a first characteristic, the intensity of the detectable scattered light is dependent upon the physical and geometrical attributes of the defect, such as the size, shape, orientation and/or index of refraction of the particle. As a second characteristic, the intensity of the detectable scattered light is dependent upon the light intensity of the surrounding environment, or background, of the wafer. As a third characteristic, the intensity of the detectable scattered light is dependent upon the spatial relation of the light source and the detector relative to the substrate.

Accordingly, different approaches have been utilized to improve the effectiveness in which an inspection system can detect particles disposed on a substrate.

One approach which has been used to improve the effectiveness in which an inspection system can detect particles disposed on a substrate, thereby increasing the overall defect count of the system, is simply to analyze the detectable scattered light at different points of observation using multiple detectors. In this manner, with each observation point offering a different perspective on the scattered light, the ability of the inspection system to be able to distinguish the defect from the background of the wafer is enhanced.

The use of multiple detectors in an inspection system to analyze detectable scattered light at different points of observation introduces numerous drawbacks.

As a first drawback, it should be noted that no single multi-detector configuration will optimize the detection capability of the inspection system for all types of defects and substrates. Rather, one multi-detector configuration that is optimized for one substrate may lead to totally unacceptable results for another substrate, thereby rendering the inspection system unreliable.

As a second drawback, it should be noted that the capability to reconfigure the detectors on demand (e.g. after a change to a substrate with a distinctively different background scatter signature) is highly labor intensive, which is undesirable. Specifically, the optimization process for reconfiguring the detectors requires the implementation of a complicated search algorithm, the cumbersome repositioning of the detectors and the implementation of hardware for suppressing background light.

As a third drawback, it should be noted that the use of multiple detectors in an inspection system to analyze detectable scattered light at different points of observation is useless if the particle is not properly illuminated by the light source.

In U.S. Pat. No. 5,046,847 to T. Nakata et al, there is disclosed a method and apparatus for detecting foreign matter on a sample by illuminating a stripe-shaped region with linearly polarized light. Some of the light reflected by the sample is intercepted by a light intercepting stage, and the rest of the light reflected by the sample, which passes through the light intercepting stage is directed to a detecting optical system, to be detected by a photodetector. The sample is illuminated obliquely at a predetermined angle with respect to a group of straight lines constituting a primary pattern on the sample. The angle is selected so that the diffraction light reflected by the group of straight lines does not enter the detecting optical system. A polarizing spatial filter using a liquid crystal element may be disposed in a predetermined restricted region in a spacial frequency region, or Fourier transformation plane, within the detecting optical system. The light scattered by the sample may further be separated in the detecting optical system into partial beams having different wave orientation characteristics, which characteristics are detected by a number of one-dimensional solid state imaging elements. The signals are processed by a driver, adder, and quantizer in synchronism with the one-dimensional solid state imaging elements.

It should be noted that the inspection system disclosed in U.S. Pat. No. 5,046,847 to T. Nakata et al suffers from a notable drawback. Specifically, during the scanning process, the multiple light sources move dependently of one another and, as such, are orientated to have identical approach angles. The use of identical approach angles for each light source ensures that particles illuminated by each light source have common coordinates on the detector. However, it has been found that, by using identical approach angles for each light source, the effectiveness of each light source to illuminate particles is compromised. Specifically, the optimal approach angle for the first light source may be a less than optimal approach angle for the second light source. As a consequence, the benefit in using multiple light sources to increase the intensity of the illumination of particles on the wafer is not maximized, which undesirable.

In U.S. Pat. No. 4,966,457 to F. Hayano et al, there is disclosed a defect inspecting apparatus for determining the presence of a defect element adhering to either of the front and back surfaces of a thin film-like object to be inspected (the object having a light-transmitting property), wherein a single light beam made up of two light beams of different wavelengths is applied to a surface of the object and the incident angle of the combined light beam is varied. A first photoelectric detector receives light reflected by or transmitted by the object, and a second photoelectric detector receives light scattered by the defect element. A discriminator determines the surface of the object to which the defect element adheres based on detection outputs of the photoelectric detectors.

Other patents of interest include U.S. Pat. No. 4,898,471 to J. P. Stonestram et al, U.S. Pat. No. 5,355,212 to K. B. Wells et al and U.S. Pat. No. 5,625,193 to S. V. Bronde et al.

SUMMARY OF THE INVENTION

It is an object of the present invention to provide a new and improved method and apparatus for inspecting a surface of semiconductor wafer having repetitive patterns for pattern defects and/or contaminant particles.

It is another object of the present invention to provide a new and improved method and apparatus for inspecting a surface semiconductor wafer having repetitive patterns for pattern defects and/or contaminant particles using scattered light.

It is yet another object of the present invention to provide a method and apparatus as described above which improves the overall detection count of pattern defects and/or contaminant particles on the surface of semiconductor wafer.

It is still another object of the present invention to provide a method and apparatus as described above which illuminates a portion of the surface on the semiconductor wafer with multiple light beams for detection of pattern defects and/or contaminant particles.

It is another object of the present invention to provide a method and apparatus as described above which has a limited number of parts and which is easy to use.

It is a further object of the present invention to provide a method and apparatus as described above for inspecting a surface of a semiconductor wafer having repetitive patterns for pattern defects and/or contaminant particles using multiple light beams to illuminate a portion of the surface, detecting light scattered from the surface as the semiconductor wafer is moving and masking off light scattered from the pattern on the surface.

It is another object of the present invention to provide a method and apparatus as described above which enables the simultaneous use of continuous motion imaging, for high speed detection with the flexibility of multi-directed, variable angle illumination, for enhanced sensitivity.

Accordingly, there is provided as per one feature of the invention an apparatus for detecting the presence of pattern defects and/or contaminant particles on a surface of a semiconductor wafer having repetitive patterns, said apparatus comprising a light source adapted to produce a first beam of light and a second beam of light, said first beam of light being disposed to illuminate a first stripe shaped region on the surface of the semiconductor wafer at a first approach angle which is angularly adjustable and a first angle of incidence which is angularly adjustable, said second beam of light being disposed to illuminate a second stripe shaped region on the semiconductor wafer at a second approach angle which is angularly adjustable and a second angle of incidence which is angularly adjustable, the first approach angle and the first angle of incidence of said first beam of light being adjustable independent of the second approach angle and the second angle of incidence of said second beam of light, respectively, the two stripe shaped regions intersecting on the surface, a CCD camera operating in a time delayed integration (TDI) mode, an imaging lens for imaging at least a portion of an area on the surface containing at least a portion of said two striped shaped regions illuminated onto said CCD cameras, as said semiconductor wafer is moving using scattered light, said imaging lens having a Fourier plane, and a filter disposed in the Fourier plane of said imaging lens for masking off the diffraction pattern produced by the background scatter from the surface of the semiconductor wafer.

According to another feature of the invention, the CCD camera has a square array sensor.

According to a further feature of the invention there is also provided a method for detecting the presence of contaminant particles and/or pattern defects on a surface of a semiconductor wafer having repetitive patterns, said apparatus comprising illuminating two stripe shaped regions on the semiconductor wafer with first and second beams of light, said first beam of light striking the semiconductor wafer at a first approach angle which is angularly adjustable and a first angle of incidence which is angularly adjustable, said second beam of light striking the semiconductor wafer at a second approach angle which is angularly adjustable and a second angle of incidence which is angularly adjustable, said first approach angle and said first angle of incidence being adjustable independent of said second approach angle and said second angle of incidence, respectively, setting said first and second approach angles to maximize the detection of defects of interest, positioning a CCD camera operating in a time delayed integration (TDI) mode above the semiconductor wafer for detecting at least some of the light scattered from the two regions illuminated but not specularly reflected light, providing an imaging lens for imaging an area on the surface containing a portion of the two regions illuminated onto the CCD camera as the semiconductor wafer is moving, providing a filter in the Fourier plane of the imaging lens for masking off the diffraction pattern produced by the background on the semiconductor wafer from the two beams of light adjusting said angle of incidence of the other beam of light so that the diffraction pattern formed by the other beam of light in the Fourier.

According to another feature of the invention the CCD camera has a square array sensor.

Various other features and advantages will appear from the description to follow. In the description, reference is made to the accompanying drawings which form a part thereof, and in which is shown by way of illustration, a specific embodiment for practicing the invention. The embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF THE PREFERRED EMBODIMENT

The present invention is directed to a method and apparatus for detecting contaminant particles and/or pattern defects on a surface of a semiconductor wafer having repetitive patterns which enables the simultaneous use of continuous motion imaging, for high speed detection, with the flexibility of multi-directed variable angle illumination for entranced sensitivity. In continuous motion imaging, the wafer is moving while you get your information as opposed to step and repeat where the wafer is stationary when information is being collected.

The present invention accomplishes this by a technique which involves illuminating the surface simultaneously from multiple directions (i.e. at multiple approach angles). This enhances the overall detection count because it increases the probability of preferentially exciting any defect of interest. As will be discussed below, however, the semiconductor wafer can only be illuminated from a finite number of directions (e.g. a continuous ring illuminator, commonly used on microscopes, could not be tolerated). The present invention further involves detecting the scattered light from the surface as the semiconductor wafer is moving using a CCD camera having a square array sensor and operating in a time delayed integration TDI mode.

The background produced using multiple approach angles is the sum of the background produced by each illuminating beam. As such, without implementing a technique to suppress the combined background, the background could easily diminish any gain realized through the optimally-directed illumination of the defect in question.

Accordingly, one feature of the present multi-approach illumination scheme lies with the operator being given independent control over the angle of incidence of each beam. By adjusting the angle of incidence of one of the beams, the operator can shift the background diffraction pattern from that beam, if necessary, so that it overlaps the background diffraction pattern from the other beam. As a result, the diffraction pattern from both beams can be masked in the Fourier plane of the collection lens using a spatial filter having bars sized to mask off the diffraction pattern produced by only one of the two beams. This is extremely important because it permits maximum transmission of the actual "defect" signal. If the two approach angles are symmetrical about a common axis, then the two background diffraction patterns will overlap at the outset and adjusting the angle of incidence of one of the light beams to shift its background diffraction pattern will not be necessary.

The multi-approach illumination scheme of the present invention can be implemented using beams originating either from multiple sources or the same source. In the system subsequently described herein, the beams originate from a single source.

According to another feature of this invention, detection of particles and/or pattern defects is based on the use of time-delayed-integration (TDI), which is a well-known technique for synchronously transferring the charge on a CCD imaging sensor so as to achieve both extended integration and continuous motion imaging. It is an inherently high-speed technique because, unlike full-frame or frame-transfer modes of CCD imaging, integration and readout are performed simultaneously. The TDI technique is most commonly used in web inspection.

As is known, standard TDI sensors are rectangular CCD arrays, typically ranging from 512 to 2048 pixels in width (horizontal dimension) by 64 to 96 pixels in depth (vertical dimension). They function basically like linear CCD arrays of the same width with the exception that, because their vertical line transfer is synchronized to the moving object under examination, their output reflects a corresponding 64–96× increase in integration without compromising inspection throughput. In applications where the illuminated region is at least as wide as the sensor's field of view, TDI enhances the signal by the same factor.

Figure 1:
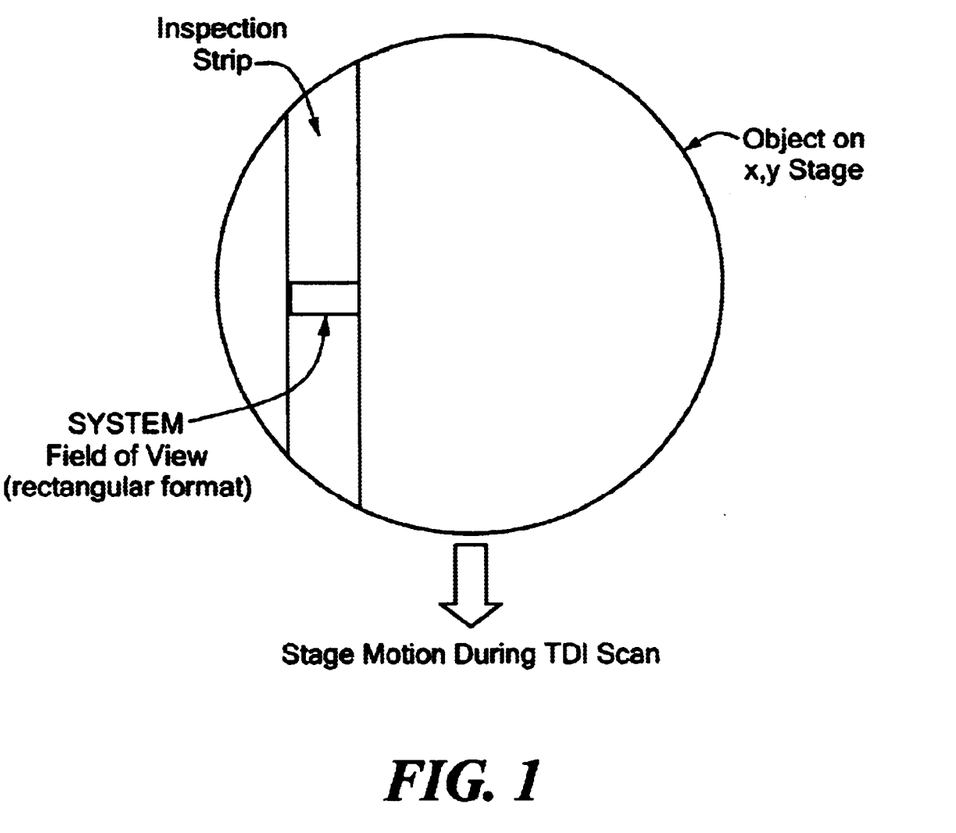
FIG. 1 is an illustration showing how an extended object has been examined in the past using a standard TDI sensor, i.e. a sensor having a rectangular CCD array.

The inspection of an extended object with a single TDI sensor having a rectangular CCD array has been accomplished in the past via multiple "strip" scanning, see FIG. 1. That is, after one full strip of the sample is scanned by translating it through the field of view, the sample is laterally stepped and the process is then repeated for the adjacent stripe. This process continues until the entire sample, strip by strip, is inspected. The sensor's width and the optical magnification set the scan width. In bi-directional sensors, scanning can be done in both directions. With such a sensor, the scan direction is simply reversed following the completion of one strip. In unidirectional sensors, scanning is only possible in one direction; this implies that the sample must be rapidly brought back to the home position, a process commonly referred to as flyback, prior to the scanning of the next strip.

Figure 2:
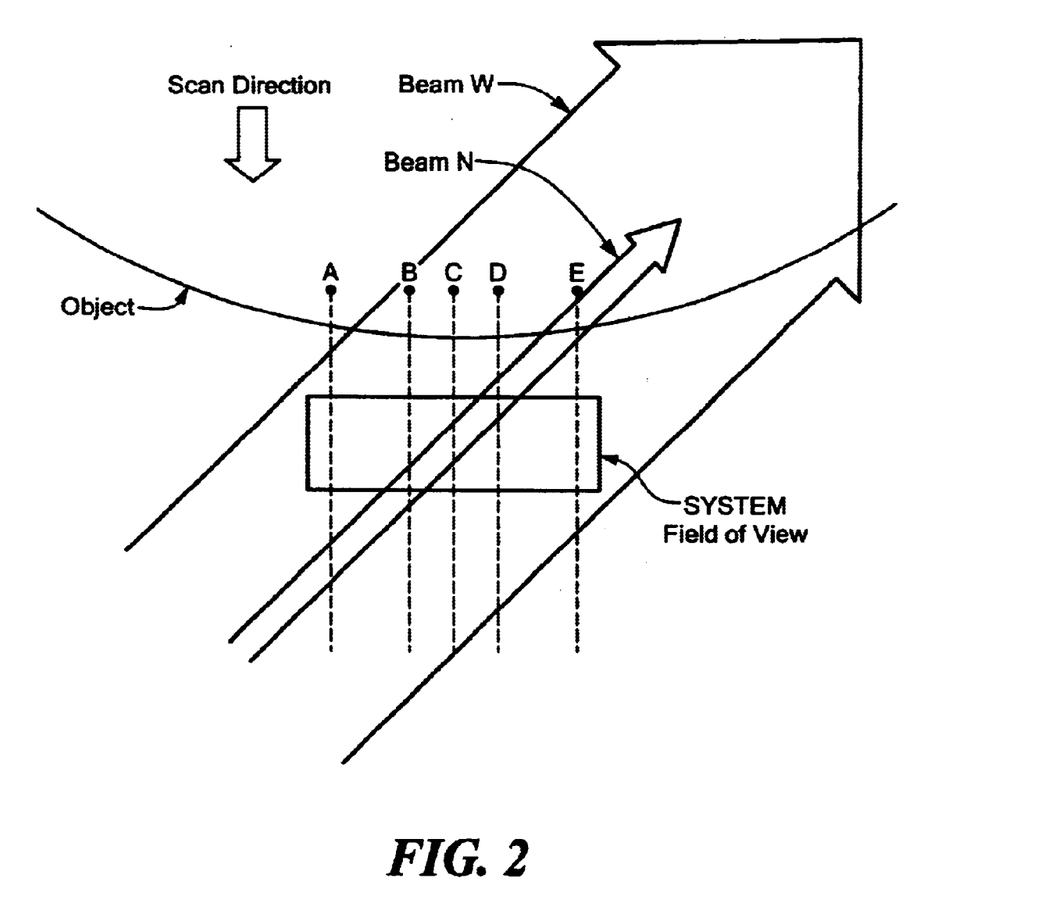
FIG. 2 is an illustration showing two light beams, each centered on the field of view of a standard, i.e. rectangular CCD array TDI sensor at the same azimuthal angle.

While multi-directed, variable-angle illumination can be realized with the use of standard TDI sensors (i.e. rectangular CD array), it necessitates the use of wide illumination beams. That is, the width of each beam must be large enough to provide uniform illumination across the entire field. Consider, for example, the case depicted in FIG. 2 where five collinear points, A through E, on the sample traverse the path of two illumination beams, each centered on the field of view at the same azimuthal angle. Furthermore, let one beam N be narrow and the other W wide. In contrast to the wide one. W, the narrow beam N will yield an image that is dark along the two field edges. That is, while the narrow beam N, does in fact illuminate points A and E, it does not do so when they are in the field of view. Hence C and to a lessor extend B and D will be the only ones visible in the resultant image. In the case of the wider beam W, all 5 points will be visible.

In order to satisfy the requirement of uniform illumination, each beam may be expanded to the extent that they overfill the field of interest; i.e. the larger the azimuthal angle, the wider the beam must be. This not only reduces the illumination density but, as in the case of patterned semiconductor wafers, may increase background scatter via the illumination of regions outside the area of concern. Both lead to a reduction in the signal-to-noise ratio, hence detectability.

This present invention proposes the extension of the TDI charge transfer technique to higher aspect ratio CCD arrays, such as square array (i.e. 1024×1024 pixels). The beauty of this approach is that it enables the use of multi-directed, variable-angle illumination with narrow beams NB1 and NB2 of illumination, see FIG. 3. This use of narrow beams minimizes the inadvertent illumination of peripheral regions on the sample and it maximizes the illumination density in the regions of interest.

The aspect ratio of the CCD sensor dictates the range over which the azimuthal angle can be varied. Consider, for example, the case depicted in FIG. 3 where a TDI sensor with a square format is employed. For simplicity only two beams are shown. The use of a sensor with a square format sensor permits the azimuthal angle of either beam to be varied within the range +/–45 degrees. The extent to which the beams can approach the 45 degree range limits is determined by their width; i.e. the thinner the beams, the closer they can approach the range limits and still yield uniform illumination across the field. Angle 45 or –45 degrees is attainable only in the limit of zero beam width.

Figure 4:
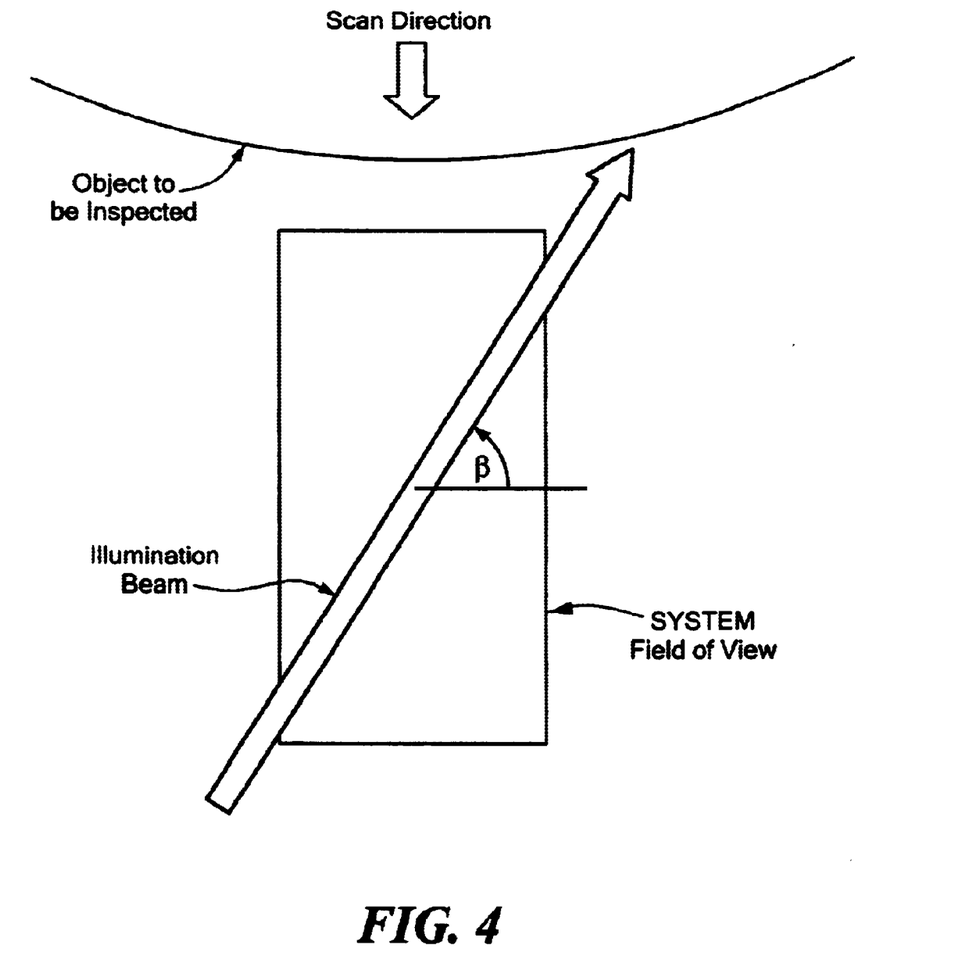
FIG. 4 is an illustration showing how the concept of this invention can be used with an azimuthal range of + or −63 degrees.

The use of sensors with higher aspect ratios (i.e. depth>width) can enable the use of even higher azimuthal angles, if desired. For example, the use of a 1024(H)×2048 (V) sensor (i.e. 2048 lines of TDI integration and a field width of 1024 pixels) has an aspect ratio of 2 and hence will permit illumination with an illumination beam within the azimuthal range β+/−63 degrees, as shown in FIG. 4. In FIG. 4 only a single directed beam, projected onto the object plane is depicted.

The use of narrow beams also reduces the uniformity constraint to a one-dimensional problem. That is, one then needs only to be concerned with spatial uniformity along the direction of propagation. Non-uniformity along the orthogonal axis (e.g. due to the gaussian profile of a laser beam) is tolerated because of the fundamental nature of signal integration utilized in the TDI technique.

As stated at the onset, one of the main attributes of the conventional TDI technique over single line scan imaging is its capability of extended integration. That is, providing that there is ample illumination coverage (i.e. broad area of illumination), signal amplification will be proportional to the number of vertical charge transfers. Amplification by extended integration, in striking contrast, is not however the primary objective of this invention. In fact, it is even desirable, from the point of view of maximizing the permissible range of azimuthal angles, to minimize the width of the illuminating beams, which would preclude any amplifications.

The main attribute of TDI, as specifically applied to this invention, is its ability to synchronously transfer charge irrespective of the location of the illumination in the field of view. For illustration, refer back to FIG. 3 and consider the 2 collinear points, labeled A and B, on the moving object. Despite charge integration across the full sensor, signal integration "effectively" occurs for only a small fraction of the total time that it takes to traverse the field; i.e. it occurs only when the point in question specifically traverses either of the two illumination beams. Given the nature of the directed illumination, the means that A will be simultaneously illuminated by both breams midway through its traverse of the field. B, on the other hand, will be illuminated by one of the beams about 40% of its way across the field and then by the other when it is nearly three-quarters of its way across the field. The beauty of this invention is that it accommodates such a difference in illumination timing, and hence enables the use of this desired type of illumination. That is, in the end, both A and B will have experienced the same total level of illumination.

It is generally a straightforward task to modify any wide-format CCD to run in the TDI mode. It typically involves only timing modifications (i.e. no design modifications are required to the CCD chip itself).

Figure 5:
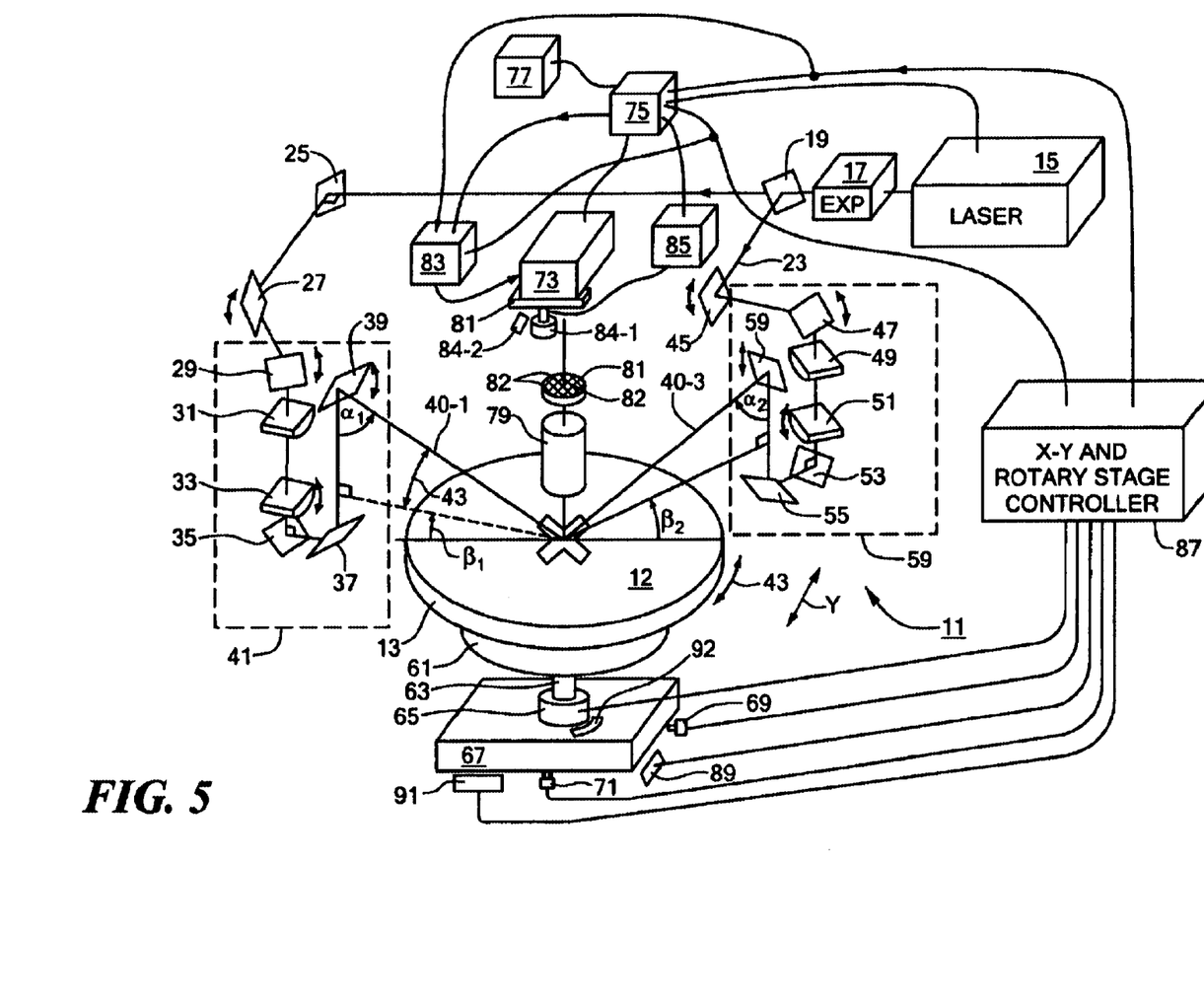
FIG. 5 is a schematic representation of an embodiment of an apparatus constructed according to the teachings of the present invention for detecting the presence of pattern defects and/or contaminant particles on the surface of a semiconductor wafer having repetitive patterns.

In accordance with this invention, there is shown in FIG. 5 an apparatus constructed according to the teachings of the present invention for detecting pattern defects and/or particles on front surface 12 of a semiconductor wafer 13, front surface 12 having repetitive patterns, using the principle of scattered light, the apparatus being identified by reference numeral 11.

Apparatus 11 includes a laser light source 15, which may be for example a frequency doubled YAG laser. Light source 15 produces a beam of light which is expanded by a beam expander 17. The expanded light then strikes a beamsplitter 19 where the expanded light is split into a transmitted beam of light 21 and a reflected beam of light 23.

Transmitted beam of light 21 is deflected off a first folding mirror 25 which changes its direction, a first gimbal mirror 27 and a second gimbal mirror 29. Gimbal mirror 27 is fixed in space but is angularly adjustable. Similarly, it should be noted that gimbal mirror 29 is angularly adjustable.

Light deflected off second gimbal mirror 29 passes through a pair of cylindrical lenses 31 and 33, is deflected off a pair of folding mirrors 35 and 37 and then is deflected off a galvo mirror 39. The light beam 40-1 deflected off galvo mirror 39 strikes wafer 13 at a first approach angle $\beta_1$ and at a first angle of incidence $\gamma_1$, the light beam 40-1 from galvo mirror 39 striking surface 12 of wafer 13 constituting the first beam of light 40-1. Angle of incidence $\gamma_1$ is preferably between about 50° and 90°.

First cylindrical lens 29 focuses transmitted beam of light 21 to a point in one dimension at a location between lens 29 and lens 31 and leaves the beam collimated in the other dimension. Second cylindrical lens 31 images the point formed by first cylindrical lens 29 onto wafer 13. Second cylindrical lens 31 is mounted on a stage (not shown) that is movable up and down vertically.

Second gimbal mirror 29, lenses 31 and 33, folding mirrors 35 and 37 and galvo mirror 39 are all mounted in a first tower 41, which is shown in FIG. 5 simply as a dashed line box. First tower 41 is angularly movable around semiconductor wafer 13 in the direction shown by arrows 43 so that the approach angle $\beta_1$ of first beam of light 21 striking semiconductor wafer 13 can be changed as desired. Galvo mirror 39 is preferably mounted on a vertically movable stage (not shown) so that it can be moved vertically upward or downward, as desired, to compensate for changes made in the angle of incidence $\gamma_1$ of beam 40-1.

It should be noted that the purpose of gimbal mirrors 27 and 29 is to enable first beam of light 21 to be redirected so as to strike cylindrical lens 31 when first approach angle $\beta_1$ is changed. The reason why galvo mirror 39 is mounted on a stage that is vertically movable is to enable first beam of light 21 to illuminate the same area on semiconductor wafer 13 when first angle of incidence $\gamma_1$ is changed. Furthermore, lens 33 is also mounted on a stage (not shown) that is movable up and down vertically to compensate for vertically moving galvo mirror 39.

Figure 6:
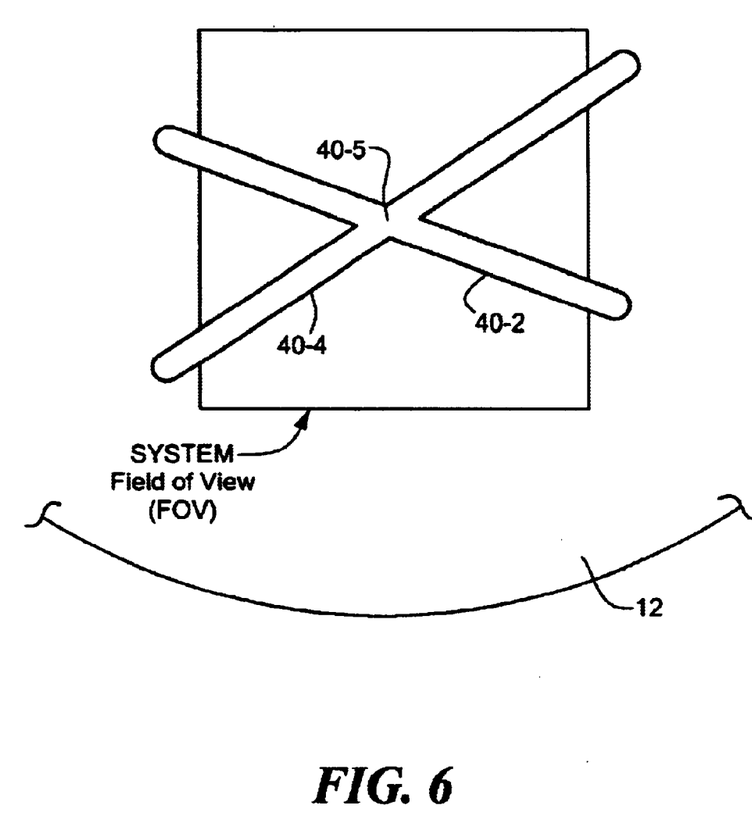
FIG. 6 is a view showing how the wafer in FIG. 5 is illuminated over two stripe shaped regions. Also, superimposed is the overall system field of view.

First beam of light 40-1 strikes surface 12 on semiconductor wafer 13 so as to illuminate a first striped shaped region 40-2, as can be seen in FIG. 6.

Transmitted beam of light 23 is deflected off a third gimbal mirror 45 and a fourth gimbal mirror 47. It should be noted that third gimbal mirror 45 is fixed in space but is angularly adjustable. Similarly, it should be noted that fourth gimbal mirror 47 is angularly adjustable.

Light deflected off fourth gimbal mirror 47 passes through a pair of cylindrical lenses 49 and 51 which are functionally and structurally identical to cylindrical lenses 31 and 33, respectively. The light passed through pair of cylindrical lenses 49 and 51 is deflected off a pair of folding mirrors 53 and 55, is deflected off a galvo mirror 57 and strikes surface 12 wafer 13 at a second approach angle $\beta_2$ and at a second angle of incidence $\gamma_2$, the light beam from galvo 57 striking wafer 13 constituting the second beam of light 40-3. Second beam of light 40-3 is angularly positioned so that when it strikes surface 13 it illuminates a second striped shaped region 40-4. First striped shaped region 40-2 intersects second striped shaped region at a common area 40-5 as can be seen in FIG. 6.

Referring back to FIG. 5, fourth gimbal mirror 47, lenses 49 and 51, folding mirrors 53 and 55 and galvo mirror 57 are all mounted on a second tower 59, which is shown simply as dashed line box. Second tower 59 is angularly movable around semiconductor wafer 13 in the direction shown by arrows 43 so that the approach angle $\beta_2$ of second beam of light 23 striking semiconductor wafer 13 can be changed as desired. Galvo mirror 57 is preferably mounted on a vertically movable stage (not shown) so that galvo mirror 57 can be moved vertically upward or downward, as desired.

Wafer 13 is seated on a holder 61 which is in the form of a vacuum chuck. Holder 61 is mounted on a vertical shaft 63 which is rotatable about its longitudinal axis A by means of a motor 65 so that wafer 13 can be rotated relative to the incident light beam to the angular position noted above where the diffracted light is at a minimum. Motor 65 is mounted on a platform (stage) 67 which is movable translationally in two mutually perpendicular directions by two linear drive motors 69 and 71 so that the surface 12 of wafer 13 can be illuminated continuously an area at a time, by the impinging beams of light as wafer 13 is moving in the Y direction.

Platform 67 may be for example an XH series X-Y stage made by Dover Instrument Corp. of Westboro, Mass. Shaft 63 and motor 65 may be, for example, a Rotary Positioner, made by Dover Instrument Corp. of Westboro, Mass.

Apparatus 11 further includes a CCD camera 73, computer 75, a display 77, an imaging lens 79, a spatial filter 81, a camera controller 83, a camera stage 84, a camera stage motor 84-1, a camera stage encoder 84-2, a camera stage controller 85 an x-y and rotary stage controller 87 and a pair of encoders 89 and 91.

CCD camera 73 is used to record an image of surface 12, using scattered light from the surface illuminated by light beams 40-1 and 40-3 and not blocked off by spatial filter 81 as wafer is moving. Computer 75, collects and processes data received from CCD camera 73 and controls the operation of all the other components in system 11. Display 77 displays the image received by CCD camera 73 which is processed, if necessary by computer 75. Imaging lens 79 collects light from an area on surface 12. Filter 81 filters out background scattered light form surface 12. Camera controller 83 controls the operation of CCD camera 73 on instructions form computer 75. Camera controller 83 receives an external line trigger on line 84 from x-y and rotary stage controller 87. Camera controller 83 controls the operation of camera 73. X-Y and rotary stage controller 87 controls the operation of motors 65, 69 and 71. Encoders 89 and 91 and 92 provide position information of holder 61 and stage 67 to controller 87. Camera stage controller 85 controls the operation of motor 84-1 which moves stage 84. Encoder 84-2 provides angular position information of stage 84.

CCD camera 73 is a CCD camera having a square array sensor and arranged to operate in a time delayed integration (TDI) mode. CCD camera 73 may be for example, a Dalso CA-D4/D7 area camera made by Dalsa Inc. modified to included a Philips FTT1010-M square frame transfer CCD image person in place of the existing image sensor in the camera and then modifying the timing electronics in the camera to enable the camera to operate in a TDI mode.

The area on semiconductor wafer 13 which is illuminated by first beam of light 40-1 and second beam of light 40-2 is imaged onto a CCD camera 73, by an imaging lens 79 using scattered light from surface 12 that is not blocked by spatial filter 81. Spatial filter 81 is disposed in the Fourier plane of imaging lens 79 to mask out background scattered light on semiconductor wafer 13 in the area illuminated. Spatial filter 81 has masking bars 82 sized to mask the background diffraction patterns formed by each beam, however, as will be hereinafter explained, the background diffraction patterns from both beams are arranged so that they overlap in the Fourier transform plane of lens 79. Thus, a mask sized and arranged to mask the background diffraction pattern formed by one beam will also mask the background diffraction pattern formed by the other beam.

Apparatus 11 is set up for use in the following manner.

First, towers 41 and 59 are angularly positioned around semiconductor wafer 13 so as to illuminate semiconductor wafer 13 at two different approach angles $\beta_1$ and $\beta_2$. The two approach angles $\beta_1$ and $\beta_2$ are independent of each other. Each approach angle is determined by examining semiconductor wafer 13 for an angular position where the signal is maximized. The angle of incidence $\gamma_1$ and $\gamma_2$ of each beam is then adjusted so that the two beams illuminate the same area on semiconductor wafer 13.

If the two approach angles are symmetrically disposed about a common axis (for example, ±45° from the x axis), then the background diffraction pattern from one beam will overlap the background diffraction pattern from the other beam and a spatial filter having masking bars sized and arranged to mask off the diffraction pattern from one beam will also mask off the diffraction pattern from the other beam.

However, if the two approach angles $\beta_1$ and $\beta_2$ are not symmetrically disposed about a common axis, (i.e. one approach angle is for example +30° from the x axis and the other approach angle is −45° from the x axis, then the two diffraction patterns will not overlap but rather will be offset relative to each other.

One possible solution to this problem is to provide a spatial filter having masking bars which are wide enough so as to mask off the diffraction lines from both beams. Another possible solution is to provide a spatial filter having masking bars for each background diffraction pattern. Both of these possible solutions are undesirable since they would result in masking off additional surface area on semiconductor wafer 13.

According to this invention, the problem of non-overlapping background diffraction patterns is solved by shifting one of the background diffraction patterns so that it overlaps the other background diffraction pattern. Shifting one of the background diffraction patterns is achieved by changing the angle of incidence γ of the light beam used to produce the background diffraction pattern. For example, the angle of incidence $\gamma_1$ of beam 40-1 can be changed by tilting galvo mirror 39 up or down. At the same time, galvo mirror 39 is moved vertically so that beam 40-1 still hits wafer 13 at the same spot.

Figure 7:
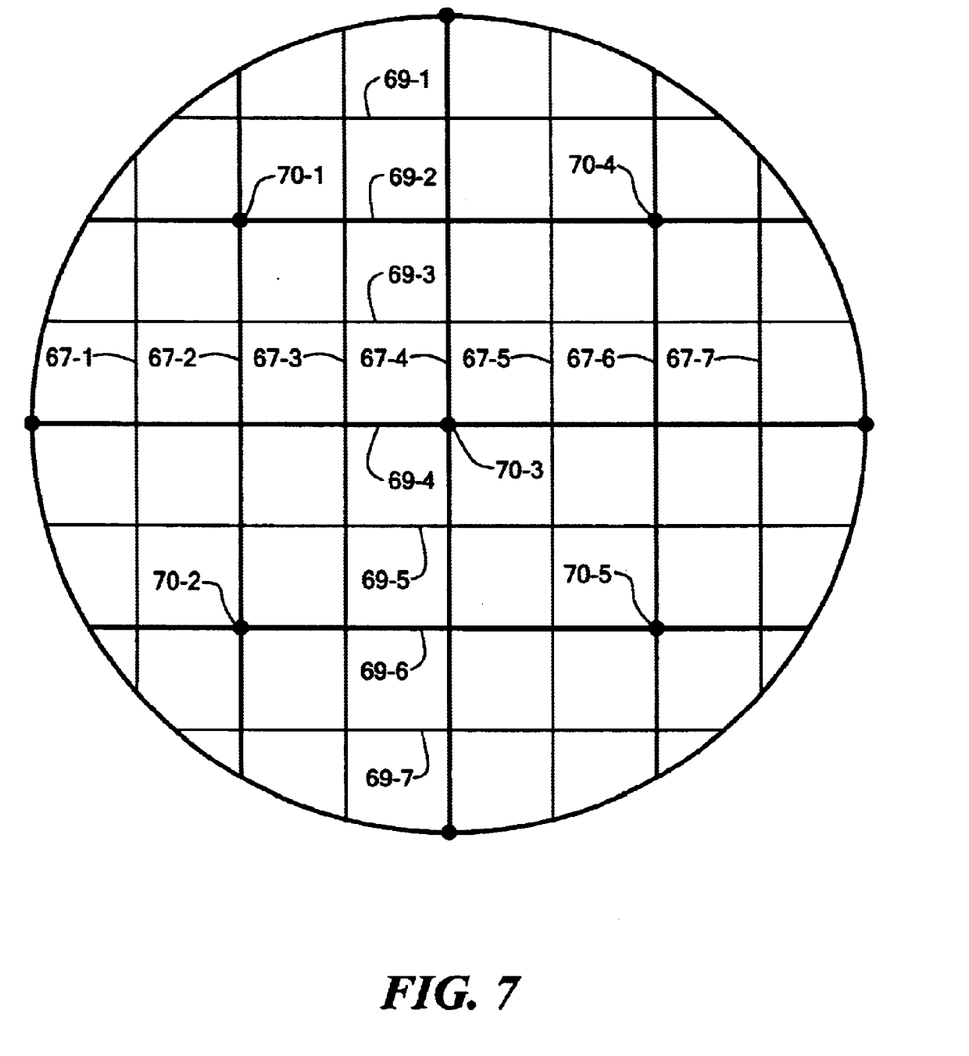
FIGS. 7 through 9 are illustrations showing how the diffraction pattern produced by one of the illuminating beams is moved relative to the diffraction pattern produced by the other illuminating beam as its angle of incidence is varied.
Figure 8:
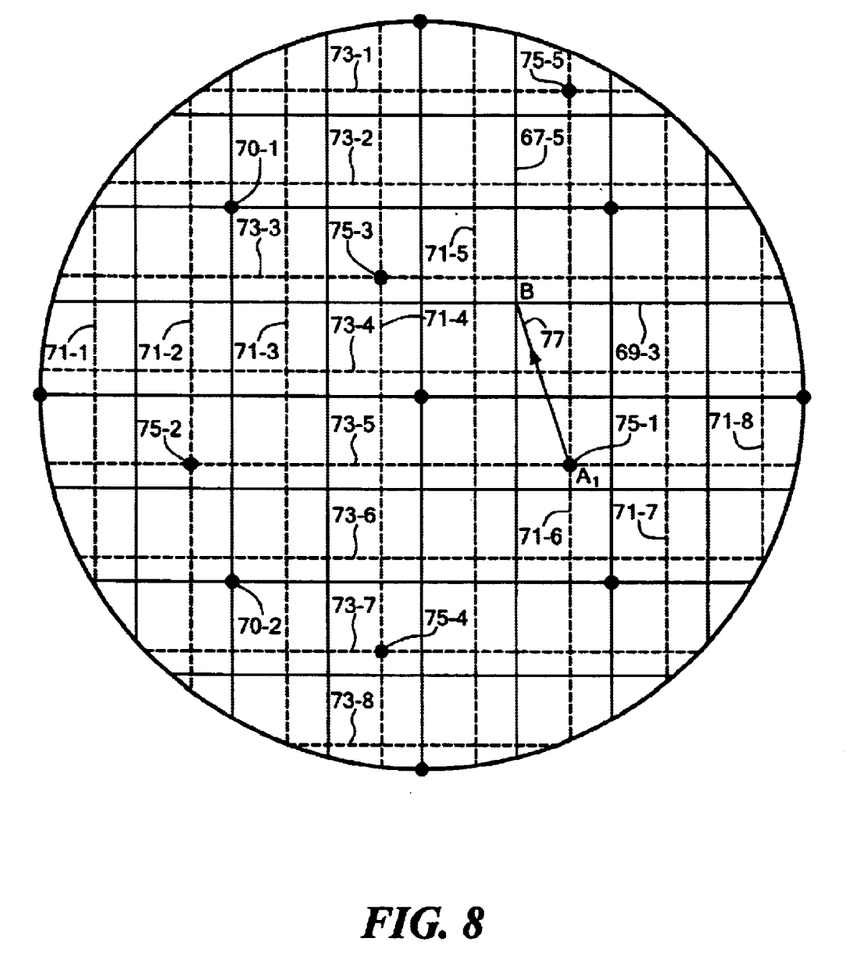
Figure 9:
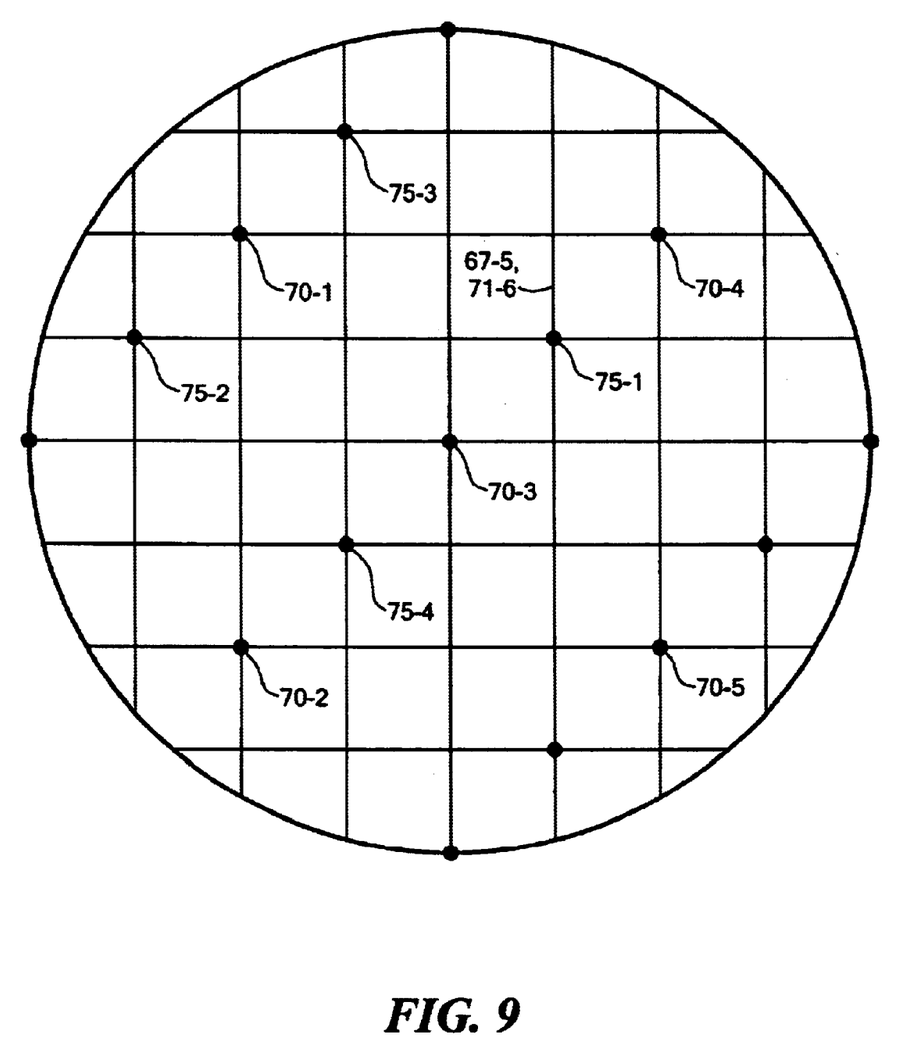

The present invention can be better understood in connection with FIGS. 7–9.

For example, a wafer 13 to be examined produces a diffraction pattern as shown in FIG. 7 from beam 40-1. What would be observed in the rear focal plane, or Fourier plane, of imaging lens 63 would be a diffraction pattern consisting of seven parallel lines 67-1 through 67-7 in the x-direction and seven parallel lines 69-1 through 69-7 in the y-direction. Also shown in FIG. 7 is a brightness of these lines that alternates with every other line. Furthermore, a bright spot 70-1 through 70-5 is shown at alternating intersections of the brighter lines.

FIG. 8 shows an additional diffraction pattern produced by beam 40-2 which strikes the wafer at a different (but non-symmetric) approach angle, the additional diffraction pattern being represented by dashed lines 71-1 through 71-8, dashed lines 73-1 through 73-8 and spots 75-1 through 75-5.

Its diffraction pattern is identical to that of beam 40-1 except for an x,y offset. The fact that its diffraction lines from beam 40-2 are still parallel to the x and y axes is due to the Wafer, not the beam's approach angle.

As noted above, the sole reason for illuminating a wafer at two particular and different approach angles is that it will maximize the detection of the defects of interest. To maximize the signal to noise and signal to background ratio, you must then reduce the background.

Obviously, one could try to use a 15×15 line mask to block these diffraction components. The problem is that the more you mask, the more you attenuate your signal. The diffraction pattern of the signal is not shown. It is orders of magnitude less intense, but more importantly, it consists of broad bands as opposed to the sharp lines and dots produced by the wafer's periodic features. Therefore, almost any kind of masking will, to some extent, affect the signal itself.

According to this invention, the diffraction pattern produced by one of the beams across the Fourier plane can be shifted by adjusting its incident angle. The direction of the shift depends upon the beam's approach angle. Suppose in the illustrated example, the shift in the diffraction pattern produced by one of the beams is in the direction indicated by the arrow 77 in FIG. 2. This means that, as the incident angle of beam 40-2 is varied, the entire diffraction pattern for beam 40-2 will move in the direction of arrow 77. At all times during this movement, however, the lines of the diffraction pattern will remain parallel to the x and y axes.

Figure 3:
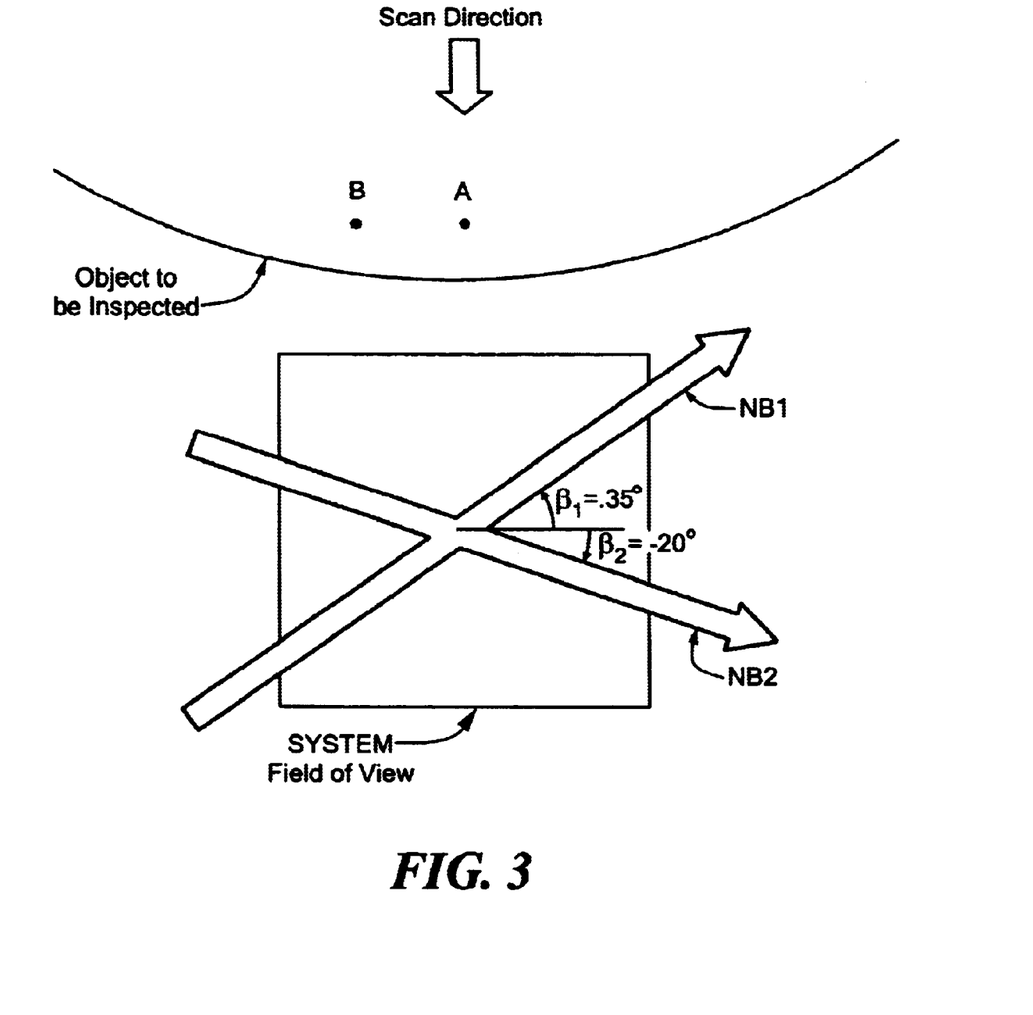
FIG. 3 is an illustration showing the use of two intersecting narrow illumination beams and a square CCD array, TDI sensor according to this invention; in the Figure the beams are depicted as being projected onto the object plane.

In the example shown above, the diffraction spot designated as 75-1 at intersection A in FIG. 3 will eventually move to the intersection of two diffraction lines 67-5 and 69-3 from beam 40-1, as designated by intersection B. The diffraction pattern produced by the two beams will then be as illustrated in FIG. 9. At this point, the same Fourier mask that would have been used if the apparatus comprised just one illuminating beam could now be used to block out the diffraction pattern from both beams. As this is a much simpler mask (i.e. 7×7 vs. 15×15 lines), there will be far less attenuation of the defect signal. The end result is a superior signal to noise ratio.

In the operation of system 11, beams 40-1 and 40-2 are directed onto surface 12 as wafer 13 is moving continuously. Imaging lens 79 images an area of wafer 13 onto a plane upon which CCD camera 73 is physically centered. That portion of the lens' imaging field, which is intercepted by CCD camera 73's sensor (sensor having the smaller dimension), defines the overall system's field-of-view (FOV).

The stripe shaped regions 40-2 and 40-4 cris-cross this FOV.

While lens 79 collects scattered light from all points within its field, it is CCD camera 73 via the TDI technique that systematically and synchronously tracks and continually integrates the scatter produced by each point on wafer 13 during the time it traverses the system's filed of view FOV.

It should be noted that it is not important that the diffraction spots of the two beams be superimposed, such as in the example noted above. The reason is that the Fourier masking bars of the present invention are of sufficient width that when they mask a line, they are also wide enough to mask the associated spots.

The embodiment shown in the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An apparatus for detecting the presence of contaminant particles on a surface of a semiconductor wafer having repetitive patterns, said apparatus comprising:

(a) means for producing a first beam of light and a second beam of light, said means comprising a laser for producing a beam of laser light and a beamsplitter for splitting up the beam of laser light into said first beam of light and said second beam of light, (b) first optical means for illuminating a first region area on the semiconductor wafer with said first beam of light, (c) second optical means for illuminating a second region on the semiconductor wafer sample with said second beam of light, (d) said first beam of light striking the semiconductor wafer at a first approach angle which is angularly adjustable and a first angle of incidence which is angularly adjustable, (e) said second beam of light striking the semiconductor wafer at a second approach angle which is angularly adjustable and a second angle of incidence which is angularly adjustable, (f) said first approach angle and said first angle of incidence being adjustable independent of said second approach angle and said second angle of incidence, respectively, (g) an imaging detector disposed above the semiconductor wafer for detecting light scattered from the area illuminated but not specularly reflected light, (h) an imaging lens for imaging said area illuminated on said imaging detector, said imaging lens having a Fourier plane, and (i) a spatial filter in the Fourier plane of the imaging lens for masking off the diffraction pattern produced by the background on the semiconductor wafer from each one of the two illuminating beams of light.

2. An apparatus for detecting the presence of contaminant particles on a semiconductor wafer having repetitive patterns, said apparatus comprising:

(a) means for producing a first beam of light and a second beam of light, (b) first optical means for illuminating a first region on the semiconductor wafer with said first beam of light, (c) second optical means for illuminating a second region on the semiconductor wafer with said second beam of light, (d) said first beam of light striking the semiconductor wafer at a first approach angle and a first angle of incidence, (e) said second beam of light striking the semiconductor wafer at a second approach angle and a second angle of incidence, (f) said first optical means including a variable angle mirror for varying the first angle of incidence, (g) said second optical means including a variable angle mirror for varying the second angle of incidence, (h) a first tower for holding said first optical means, said first tower being angularly movable so as to change said first approach angle, (i) a second tower for holding said second optical means, said second tower being angularly movable so as to change said second approach angle, (j) said first approach angle and said first angle of incidence being adjustable independent of said second approach angle and said second angle of incidence, respectively, (k) an imaging detector disposed above the semiconductor wafer for detecting light scattered from the area illuminated but not specularly reflected light, (l) an imaging lens for imaging said area illuminated on said imaging detector, said imaging lens having a Fourier plane, and (m) a spatial filter in the Fourier plane of the imaging lens for masking off the diffraction pattern produced by the background on the semiconductor wafer form both illuminating beams of light.

3. A method for detecting the presence of contaminant particles on a semiconductor wafer having repetitive patterns, said apparatus comprising:

(a) illuminating a portion of the semiconductor wafer with first and second beams of light originating from a single light source, (b) said first beam of light striking the semiconductor wafer at a first approach angle which is angularly adjustable and a first angle of incidence which is angularly adjustable, (c) said second beam of light striking the semiconductor wafer at a second approach angle which is angularly adjustable and a second angle of incidence which is angularly adjustable, (d) said first approach angle and said first angle of incidence being adjustable independent of said second approach angle and said second angle of incidence, repectively, (e) adjusting said first and second approach angles to minimize background scatter, (f) positioning an imaging detector above the semiconductor wafer for detecting at least some of the light scattered from the area illuminated but not specularly reflected light, (g) providing an imaging lens for imaging said area illuminated on said imaging detector, said imaging lens having a Fourier plane, (h) providing a spatial filter in the Fourier plane on the imaging lens for masking off the diffraction pattern produced by the background on the semiconductor wafer from a first one of the two beams of light, and (i) adjusting said angle of incidence of the other beam of light so that the diffraction pattern formed by the other beam of light in the Fourier plane overlaps the diffraction pattern formed by the first beam of light.

4. An apparatus for detecting the presence of contaminant particles on a semiconductor wafer having repetitive patterns, said apparatus comprising:

(a) a light source adapted to produce a first beam of light and a second beam of light, said first beam of light being disposed to illuminate a region on the semiconductor wafer at a first approach angle which is angularly adjustable and a first angle of incidence which is angularly adjustable, said second beam of light being disposed to illuminate another region on the semiconductor wafer at a second approach angle which is angularly adjustable and a second angle of incidence which is angularly adjustable, the first approach angle and the first angle of incidence of said first beam of light being adjustable independent of the second approach angle and the second angle of incidence of said second beam of light, (b) an imaging detector disposed to detect light scattered from the regions illuminated but not light specularly reflected from the area illuminated, (c) an imaging lens for imaging the regions illuminated on said imaging detector, said imaging lens having a Fourier plane, and (d) a spatial filter disposed in the Fourier plane of said imaging lens for masking off the diffraction pattern produced by the background of the semiconductor wafer from both beams of light.

5. An apparatus for detecting the presence of contaminant particles on a semiconductor wafer having repetitive patterns, said apparatus comprising:

(a) a first tower producing a first beam of light, the first beam of light illuminating a first region on the semiconductor wafer at a first approach angle and at a first angle of incidence, said first tower being angularly movable so as to change the first approach angle, (b) a second tower producing a second beam of light, the second beam of light illuminating a second region on the semiconductor wafer, the second beam of light illuminating the semiconductor wafer at a second approach angle and at a second angle of incidence, said second tower being angularly movable so as to change the second approach angle, said second tower being angularly movable independent of said first tower, (c) an imaging detector disposed to detect light scattered from the regions illuminated but not light specularly reflected from the area illuminated, (d) an imaging lens for imaging the area illuminated on said imaging detector, said imaging lens having a Fourier plane, and (e) a spatial filter disposed in the Fourier plane of said imaging lens for masking off the diffraction pattern produced by the background of the semiconductor wafer from both beams of light.

6. The apparatus of claim 5 wherein said first tower includes a variable angle mirror for varying the first angle of incidence.

7. The apparatus of claim 6 wherein said second tower includes a variable angle mirror for varying the second angle of incidence.

8. The apparatus of claim 7 wherein the variable angle mirror of said second tower is movable independent of the variable angle mirror of said first tower.

9. The apparatus of claim 8 wherein said first tower further comprises a gimbal mirror, a pair of lenses and a pair of folding mirrors.

10. The apparatus of claim 9 wherein said second tower further comprises a gimbal mirror, a pair of lenses and a pair of folding mirrors.

11. An apparatus for detecting the presence of contaminant particles on a surface of a semiconductor wafer having repetitive patterns, said apparatus comprising:

(a) a holder for holding said semiconductor wafer, (b) a light source adapted to produce a first beam of light and a second beam of light, said first beam of light being disposed relative to the semiconductor wafer to illuminate a first stripe shaped region on the semiconductor wafer at a first approach angle which is angularly adjustable, said second beam of light being disposed to illuminate a second stripe shaped region on the semiconductor wafer at a second approach angle which is angularly adjustable, said second stripe shaped region intersecting said first stripe shaped region, (c) a CCD camera, said CCD camera being operational in a time delayed integration (TDI) mode, said CCD camera having a sensor, (d) an imaging lens disposed above the two stripe shaped regions for imaging onto said CCD camera at least a portion at an area on the surface containing at least a portion of the two strip shaped regions using scattered light as the semiconductor wafer is moving, the imaging lens having a Fourier plane, (e) a filter disposed in the Fourier plane of said imaging lens for masking off the diffraction pattern produced by the background of the semiconductor wafer from both beams of light, and (f) means for moving said holder continuously.

12. The apparatus of claim 11 wherein the two stripe shaped regions intersect within the field of view of the system.

13. The apparatus of claim 12 wherein the two stripe shaped regions intersect at the center of the field of view of the system.

14. The apparatus of claim 11 wherein said sensor in the CCD camera is a square array sensor.

15. The apparatus of claim 11 wherein said first beam of light illuminates the first stripe shaped region at a first angle of incidence that is angularly adjustable and said second beam of light illuminates the second stripe shaped region at a second angle of incidence that is angularly adjustable.

16. The apparatus of claim 15 wherein the approach angle and angle of incidence of the first beam of light are each angularly adjustable independent of the approach angle and angle of incidence, respectively, of the second beam of light.

17. A method for detecting the presence of contaminant particles on a semiconductor wafer having repetitive patterns, said method comprising:

(a) illuminating a pair of intersecting stripe shaped regions on the semiconductor wafer, using a pair of beams of light originating from a single light source, each beam of light having an approach angle and an angle of incidence that is angularly adjustable independent of the approach angle and angle of incidence of the other beam of light, and (b) detecting at least some of the light scattered from the area illuminated but not specularly reflected light as said semiconductor wafer is moving using a lens and CCD camera having a square array sensor and operational in a time delayed integration mode.

* * * * *